(12) United States Patent
Yang

(10) Patent No.: US 8,465,443 B2
(45) Date of Patent: *Jun. 18, 2013

(54) MASSAGING APPARATUS

(76) Inventor: Tsung-Hsun Yang, Taichung Hsien (TW)

( * ) Notice: Subject to any disclaimer, the term of this patent is extended or adjusted under 35 U.S.C. 154(b) by 569 days.

This patent is subject to a terminal disclaimer.

(21) Appl. No.: 12/719,401

(22) Filed: Mar. 8, 2010

(65) Prior Publication Data

US 2011/0218465 A1 Sep. 8, 2011

(51) Int. Cl.
*A61H 19/00* (2006.01)
*A61H 15/00* (2006.01)
*A61H 7/00* (2006.01)

(52) U.S. Cl.
USPC .............. 601/134; 601/101; 601/84; 601/112

(58) Field of Classification Search
USPC ...................................... 601/16, 18, 118–134
See application file for complete search history.

(56) References Cited

U.S. PATENT DOCUMENTS

| 4,157,088 | A | * | 6/1979 | Gracey | 601/57 |
| 5,165,390 | A | | 11/1992 | Fleetwood | |
| 6,283,928 | B1 | * | 9/2001 | Wang | 601/99 |
| 7,998,098 | B2 | * | 8/2011 | Yang | 601/134 |
| 2004/0267168 | A1 | | 12/2004 | Feng | |
| 2008/0262398 | A1 | * | 10/2008 | Ferber et al. | 601/98 |

FOREIGN PATENT DOCUMENTS

| DE | 102007045530 A1 | 4/2009 |
| WO | WO9959516 A1 | 11/1995 |
| WO | WO2009083781 A1 | 7/2009 |

OTHER PUBLICATIONS

European Patent Office, Search Report (Extended), EP 10153605; Jul. 27, 2010.

* cited by examiner

*Primary Examiner* — Nicholas Lucchesi
*Assistant Examiner* — Leah Stohr
(74) *Attorney, Agent, or Firm* — Bill C. Panagos; Linda D. Kennedy; Butzel Long, PC

(57) ABSTRACT

A massaging apparatus includes: a main frame including a guiding rail unit extending in a longitudinal direction, and a mounting seat mounted slidably on the guiding rail unit; a drive unit mounted on the main frame for driving the mounting seat to move along the guiding rail unit in the longitudinal direction; and a massage unit mounted on the mounting seat and including a massage rod having a head portion, and a motor having an output shaft journalled on the mounting seat and connected to the massage rod for driving eccentric rotation of the massage rod relative to the output shaft.

13 Claims, 13 Drawing Sheets

MASSAGING APPARATUS

BACKGROUND OF THE INVENTION

1. Field of the Invention

The invention relates to a massaging apparatus, more particularly to a massaging apparatus that is capable of massaging a desired area of a user's body.

2. Description of the Related Art

A conventional massaging apparatus, such as a massage chair, includes a plurality of massage members mounted in seat, back and footrest portions of a chair body. However, since the positions of the massage members 13 mounted in the seat portion 121 and the footrest 123 are fixed, massagable areas for hips and legs of a user are limited. Furthermore, such a conventional massaging apparatus cannot massage a user's body at front and lateral sides, the user's limbs at inner sides and the user's foot.

SUMMARY OF THE INVENTION

Therefore, the object of the present invention is to provide a massaging apparatus that can overcome the aforesaid drawback of the prior art.

According to one aspect of the present invention, a massaging apparatus comprises:
- a main frame including an upright guiding rail unit extending in a longitudinal direction, and a mounting seat mounted slidably on the guiding rail unit;
- a drive unit mounted on the main frame for driving the mounting seat to move along the guiding rail unit in the longitudinal direction; and
- a massage unit mounted on the mounting seat and including a massage rod having a head portion, and a motor having an output shaft journalled on the mounting seat and connected to the massage rod for driving eccentric rotation of the massage rod relative to the output shaft.

According to another aspect of the present invention, a massaging apparatus comprises:
- a main frame including
  - an upright first guiding rail unit extending in a longitudinal direction and having opposite elongate lateral rail rods spaced apart from each other in a transverse direction transverse to the longitudinal direction,
  - a second guiding rail unit mounted slidably on the first guiding rail unit, and including two parallel elongate second rail rods that extend in the transverse direction and that are disposed spacedly between the lateral rail rods of the first guiding rail unit, and
  - a mounting seat mounted slidably on the second rail rods of the second guiding rail unit;
- a first drive unit mounted on the main frame for driving the second guiding rail unit to move along the lateral rail rods of the first guiding rail unit in the longitudinal direction;
- a second drive unit for driving the mounting seat to move along the second rail rods in the transverse direction;
- a massage unit mounted on the mounting seat and including a massage rod having a head portion, and a motor having an output shaft journalled on the mounting seat and connected to the massage rod for driving eccentric rotation of the massage rod relative to the output shaft; and
- a control unit connected electrically to the first drive unit, the second drive unit and the motor of the massage unit for controlling the first drive unit, the second drive unit and the motor of the massage unit so that the head portion of the massage rod is moved to a desired position through movement of the mounting seat and the second guiding rail unit so as to contact a user's body at a desired acupuncture point and that the motor of the massage unit drives the massage rod to rotate at a desired speed.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
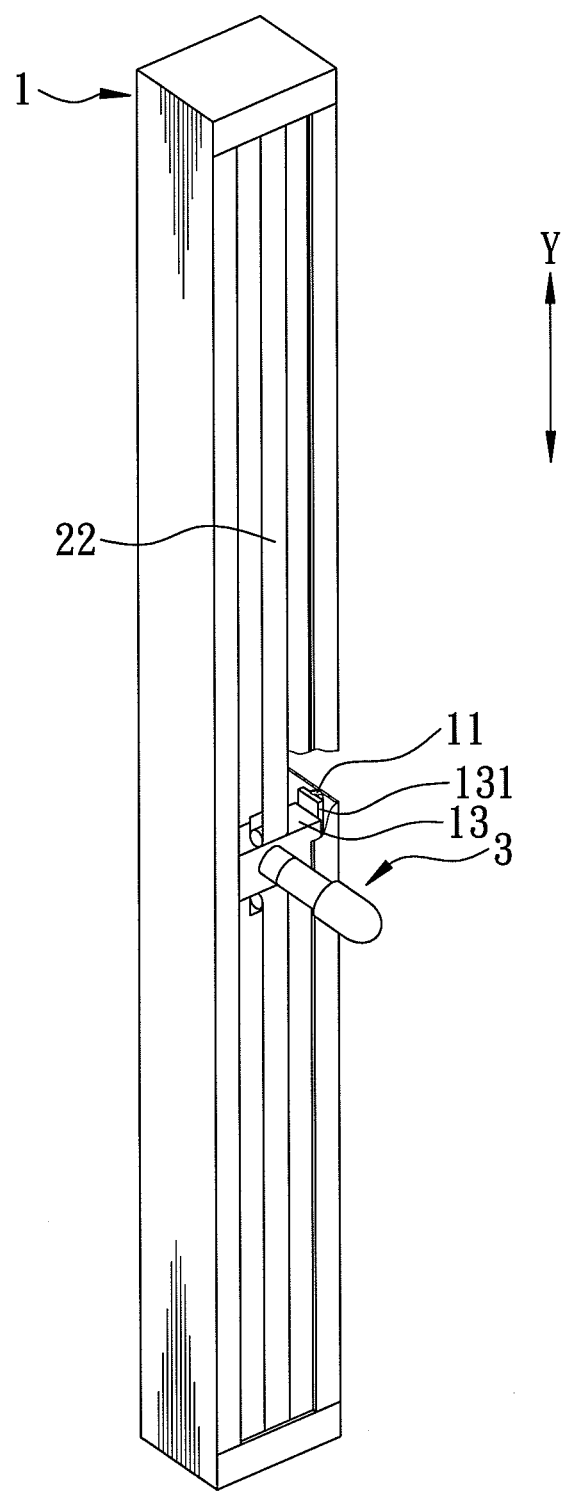
FIG. 1 is a perspective, partly cutaway view showing the first preferred embodiment of a massaging apparatus according to the present invention.

Before the present invention is described in greater detail, it should be noted that like elements are denoted by the same reference numerals throughout the disclosure.

Figure 2:
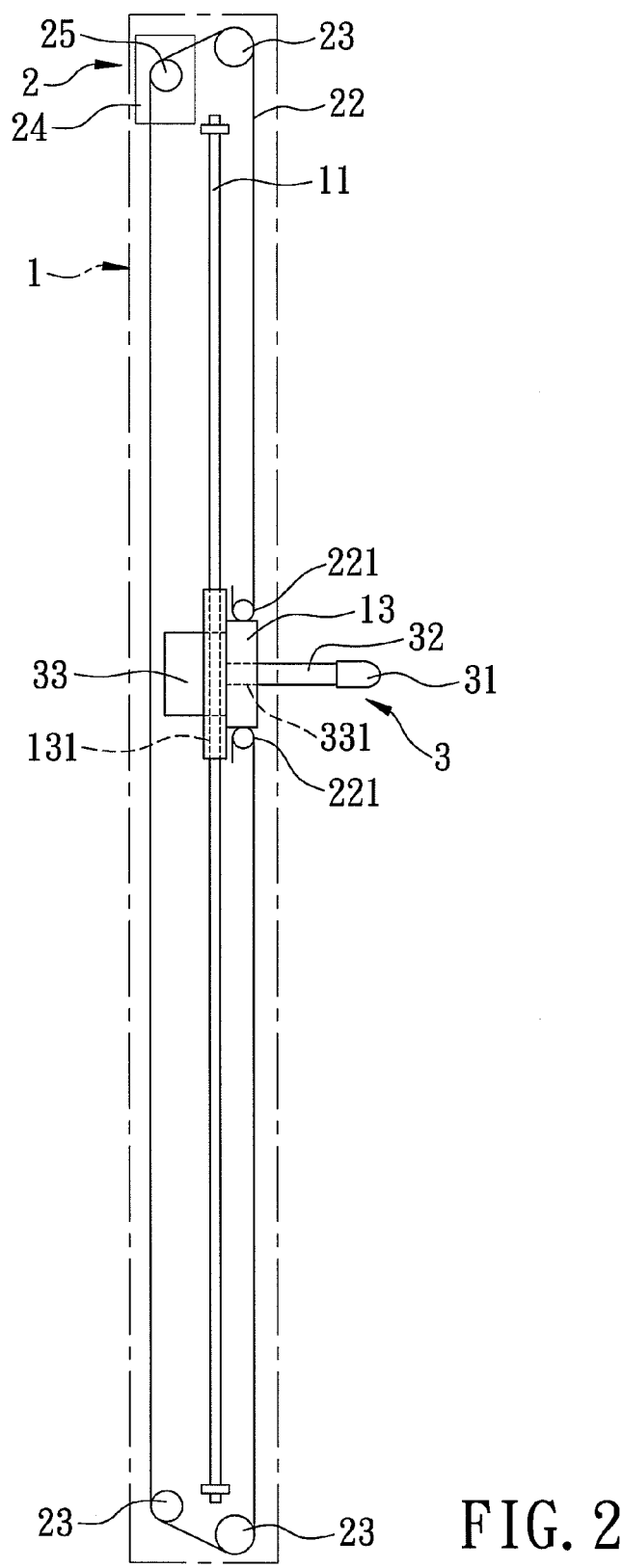
FIG. 2 is a schematic side view showing the first preferred embodiment.
Figure 3:
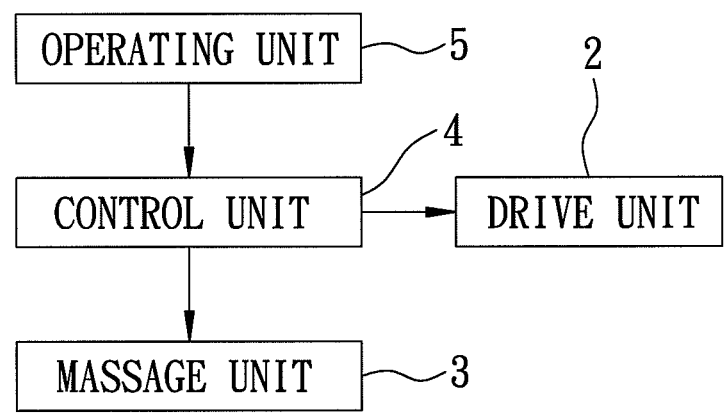
FIG. 3 is a schematic circuit block diagram illustrating the first preferred embodiment.

Referring to FIGS. 1 to 3, the first preferred embodiment of a massaging apparatus according to the present invention is shown to include a main frame 1, a drive unit 2, a massage unit 3, a control unit 4, and an operating unit 5.

The main frame 1 includes an upright guiding rail unit extending in a longitudinal direction (Y), such as a vertical direction, and a mounting seat 13 mounted slidably on the guiding rail unit. In this embodiment, the guiding rail unit includes opposite elongate lateral rail rods 11 (only one is shown in FIG. 1). The mounting seat 13 has opposite lateral sliding blocks 131 (only one is shown in FIG. 1) connected slidably to a corresponding one of the lateral rail rods 11 of the guiding rail unit.

The drive unit 2 is mounted on the main frame 1 for driving the mounting seat 13 to move along the guiding rail unit in the longitudinal direction (Y). In this embodiment, as shown in FIG. 2, the drive unit 2 includes a bi-directional motor 24, a transmission wheel set, and a transmission belt 22. The bi-directional motor 24 has a motor shaft 25 in the form of a gear and journalled on the main frame 1. The transmission wheel set includes a plurality of transmission wheels 23, and is disposed rotatably on the main frame 1, and is rotatable in response to operation of the bi-directional motor 24. The transmission belt 22 is trained on the transmission wheels 23 and the motor shaft 25 of the bi-directional motor 24, and has opposite ends 221 connected to the mounting seat 13 of the main frame 1 such that the mounting seat 13 is co-movable with the transmission belt 22.

The massage unit 3 is mounted on the mounting seat 13, and includes a massage rod 32 having a head portion 31, and a motor 33 having an output shaft 331 journalled on the mounting seat 13 and connected to the massage rod 32 for driving eccentric rotation of the massage rod 32 relative to the output shaft 331.

The control unit 4 is connected electrically to the bi-directional motor 24 of the drive unit 2, and the motor 33 of the massage unit 3 for controlling the drive unit 2 and the motor 33 of the massage unit 3 so that the head portion 31 of the massage rod 32 is moved to a desired position through movement of the mounting seat 13 so as to contact a user's body at a desired acupuncture point and that the motor 33 of the massage unit 3 drives the massage rod 32 to rotate at a desired speed.

The operating unit 5 is connected electrically to the control unit 4, and includes a plurality of input keys (not shown) that are operable so as to output a control signal to the control unit 4 such that the control unit 4 controls the bi-directional motor 24 of the drive unit 2 and the motor 33 of the massage unit 3 based on the control signal from the operating unit 5.

Figure 4:
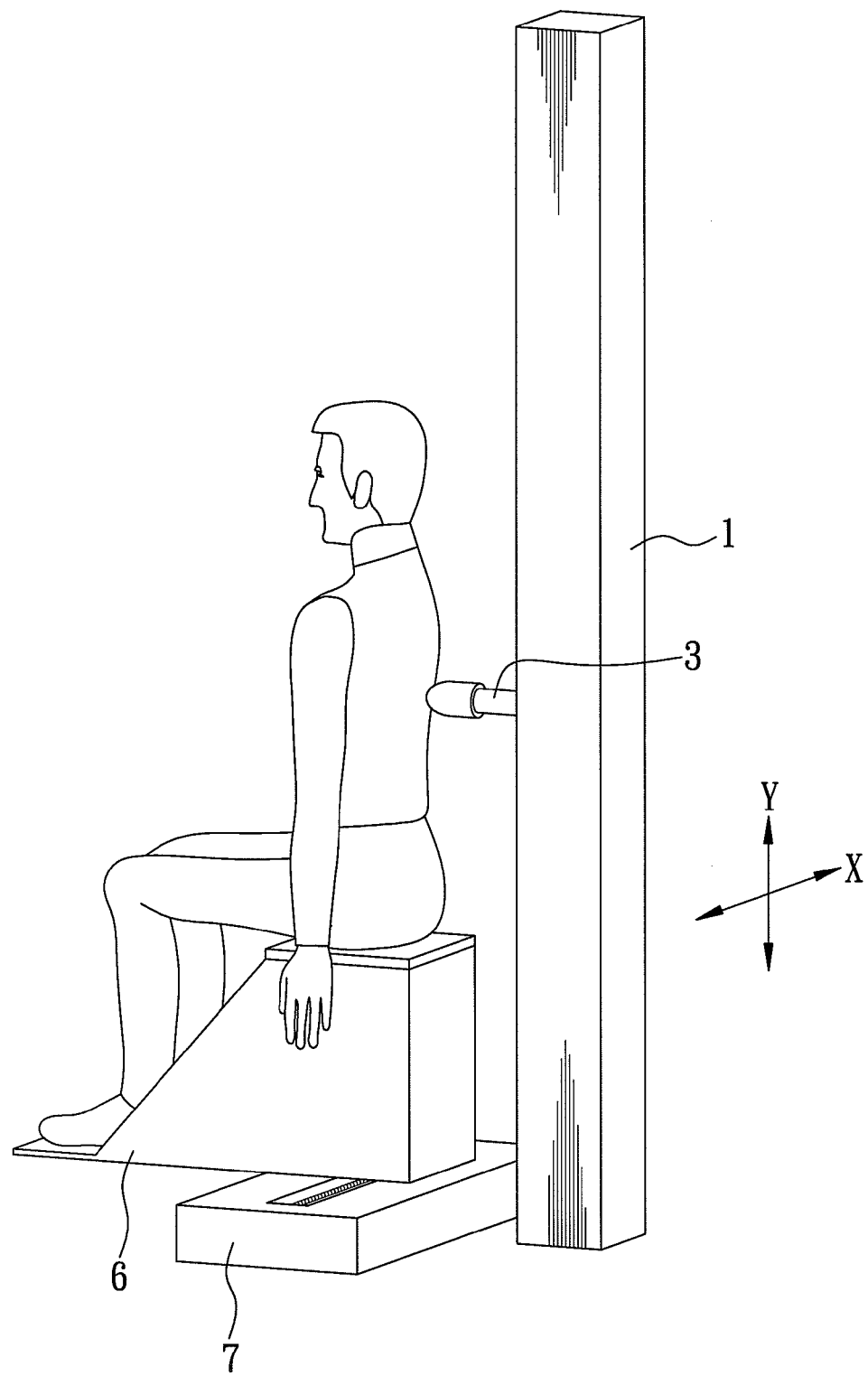
FIG. 4 is a perspective view showing the first preferred embodiment when in a state of use.
Figure 5:
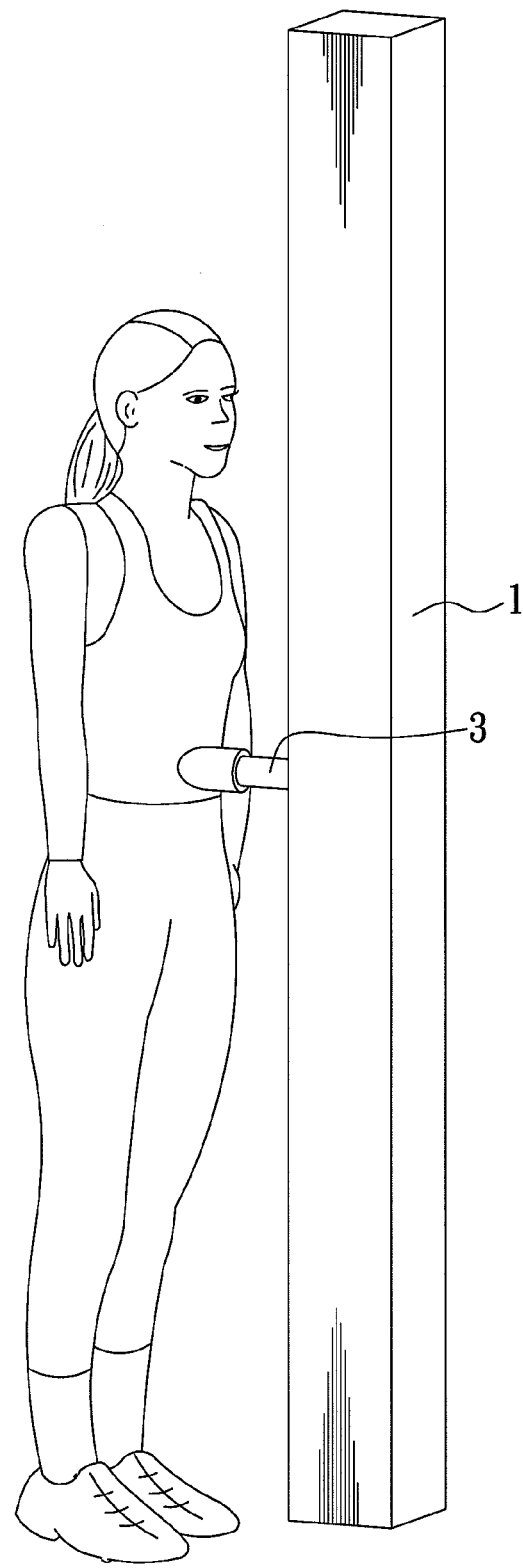
FIG. 5 is a perspective view showing the first preferred embodiment when in another state of use.

Since the head portion 31 of the massage rod 32 can be moved to a desired position in the longitudinal direction (Y), the massaging apparatus of the present invention is suitable for users with different sizes. In use, the user can adopt an appropriate posture for a desired massage area, such as a sitting posture for the user's back, as shown in FIG. 4, a standing posture for a front side of the user's body, as shown in FIG. 5, or a lying posture for the user's foot. Preferably, when the user adopts the sitting posture, a chair 6 movable relative to a base 7 in a transverse direction (X) transverse to the longitudinal direction (Y), such as a horizontal direction, is provided so as to facilitate position adjustment in the transverse direction (X) (see FIG. 4). Furthermore, during massage, the user can control a massage pressure applied to the user's body through his/her weight, thereby ensuring an approximate massage pressure.

Figure 6:
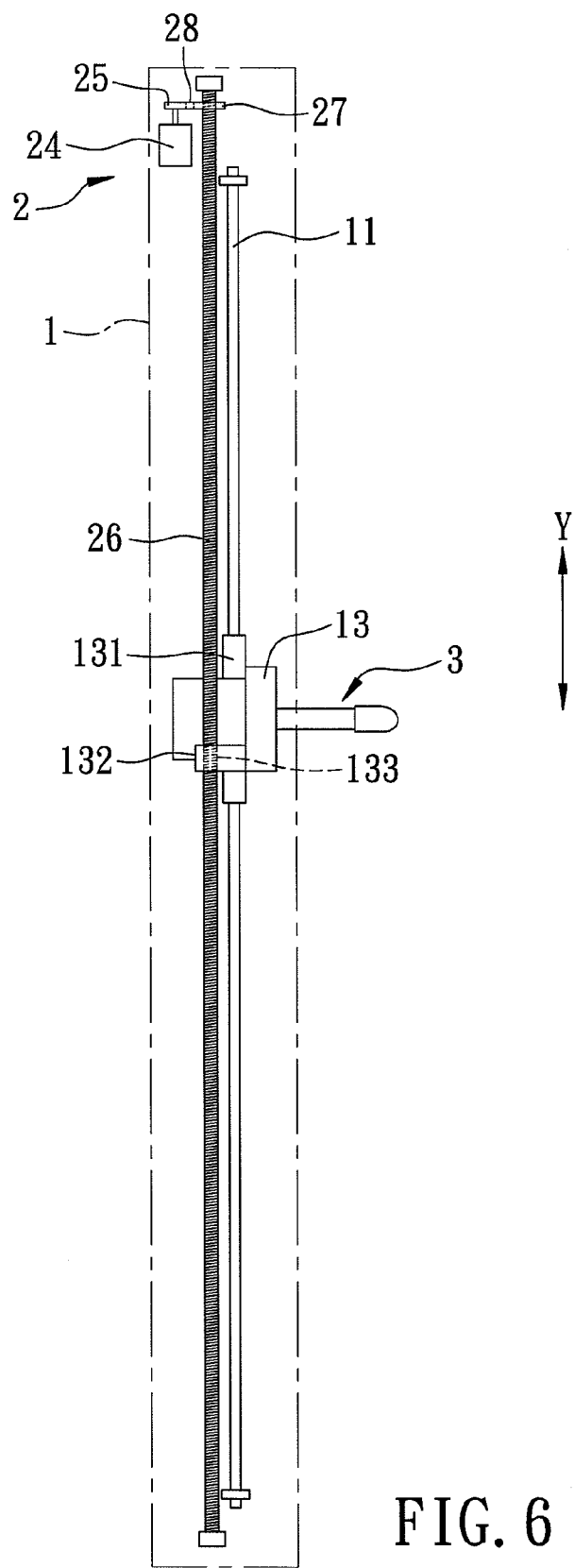
FIG. 6 is a schematic view showing the second preferred embodiment of a massaging apparatus according to the present invention.

FIG. 6 illustrates the second preferred embodiment of a massaging apparatus according to this invention, which is a modification of the first preferred embodiment. In this embodiment, the mounting seat 13 has a connecting portion 132 formed with a threaded hole 133 therethrough that extends in the longitudinal direction (Y).

In this embodiment, the drive unit 2 includes an elongate threaded rod 26, the bi-directional motor 24, a transmission wheel 27, and a looped transmission belt 28. The threaded rod 26 is journalled on the main frame 1, extends in the longitudinal direction (Y) through the threaded hole 133 in the connecting portion 132 of the mounting seat 13, and is connected threadedly to the connecting portion 132 of the mounting seat 13. The threaded rod 26 is rotatable relative to the main frame 1 so as to drive movement of the mounting seat 13 in response to rotation of the threaded rod 26. The transmission wheel 27 is mounted on and is co-rotatable with the threaded rod 26. The looped transmission belt 28 is trained on the transmission wheel 27 and the motor shaft 25 of the bi-directional motor 24.

Figure 7:
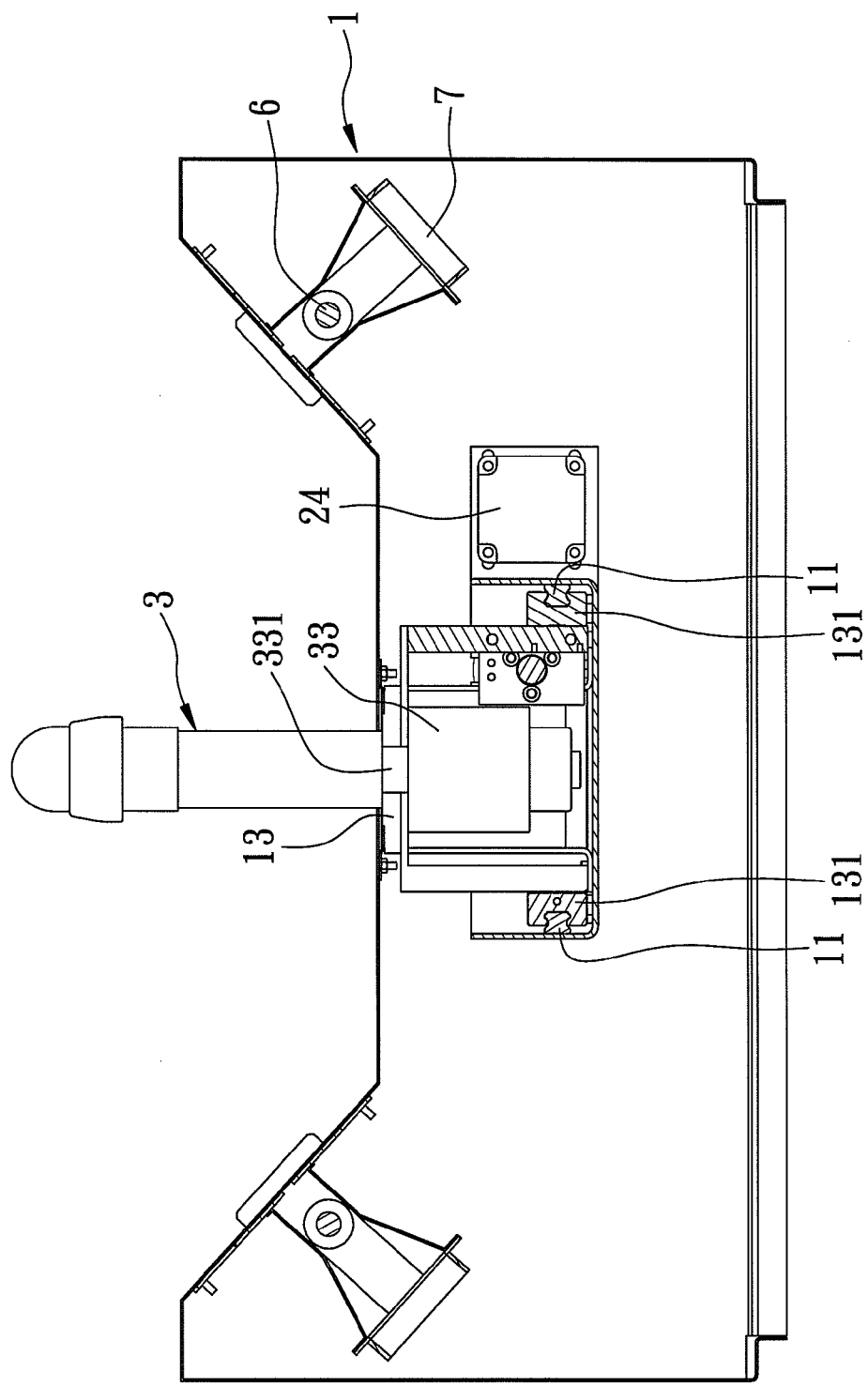
FIG. 7 is a partly schematic sectional view showing the third preferred embodiment of a massaging apparatus according to the present invention.

FIG. 7 illustrates the third preferred embodiment of a massaging apparatus according to this invention, which is a modification of the second preferred embodiment. In this embodiment, the massaging apparatus further includes a thermal generating unit mounted to the main frame 1 for radiating heat toward the user's body. In this embodiment, the thermal generating unit includes two infrared heaters 6 disposed in the main frame 1 and flanking the massage unit 3 for generating heat so as to heat air in the main frame 1, and two fans 7 disposed in the main frame 1 and corresponding respectively to the infrared heaters 6 for blowing heated air out of the main frame 1 toward the user's body.

Figure 8:
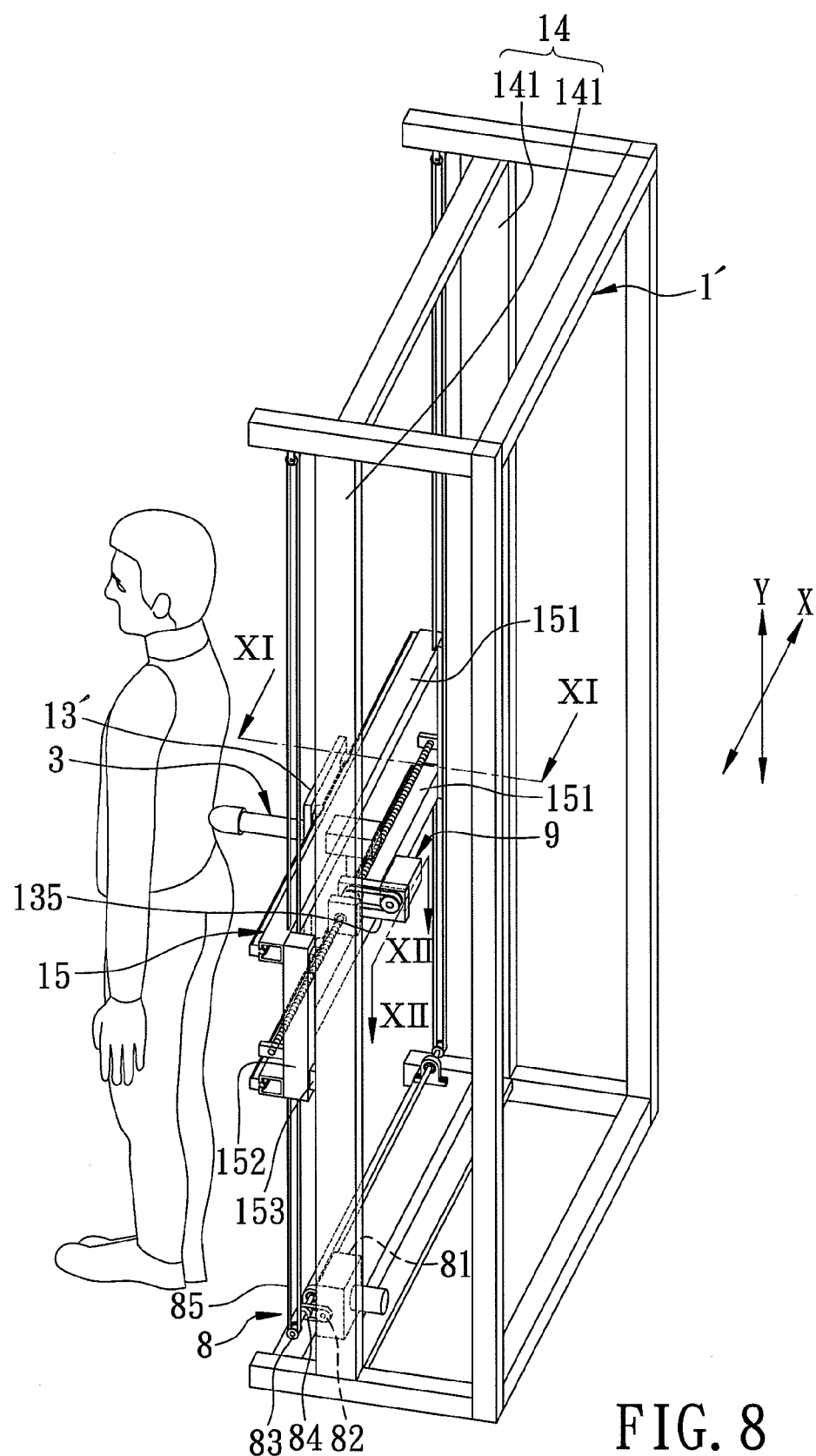
FIG. 8 is a perspective view showing the fourth preferred embodiment of a massaging apparatus according to the present invention.
Figure 9:
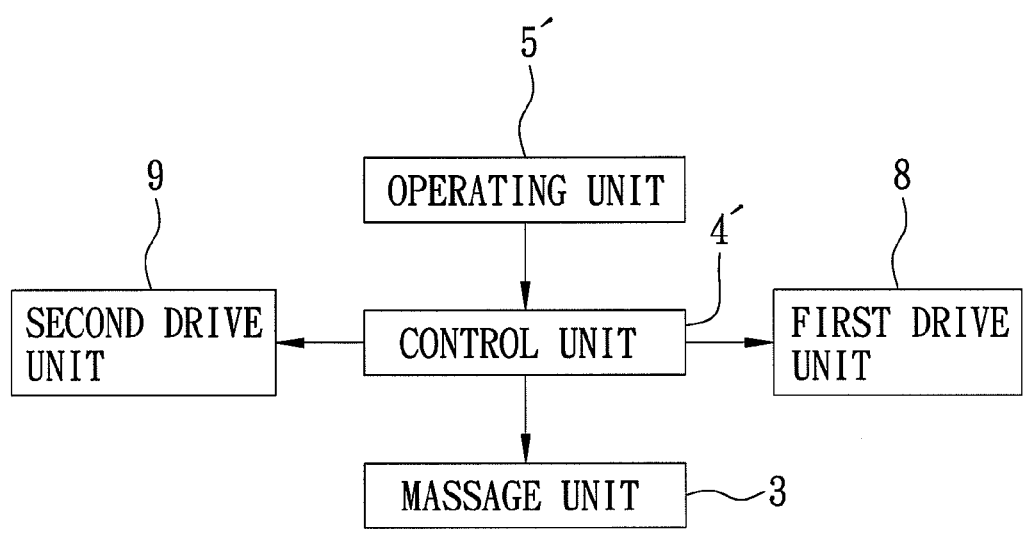
FIG. 9 is a schematic circuit block diagram illustrating the fourth preferred embodiment.

Referring to FIGS. 8 and 9, the fourth preferred embodiment of a massaging apparatus according to the present invention is shown to include a main frame 1', a first drive unit 8, a second drive unit 9, the massage unit 3, a control unit 4', and an operating unit 5'.

Figure 12:
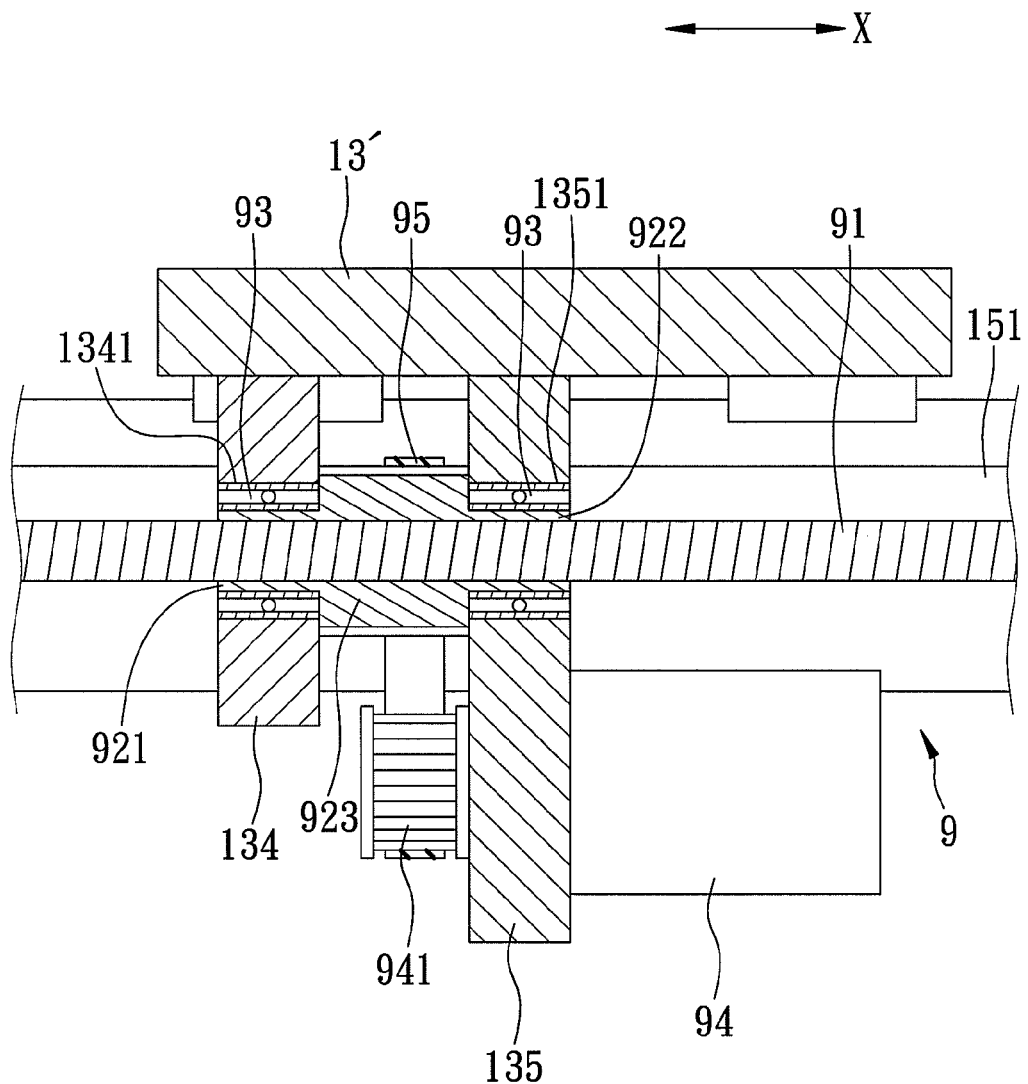
FIG. 12 is a fragmentary schematic sectional view of the fourth preferred embodiment taken along line XII-XII in FIG. 8.

The main frame 1' includes an upright first guiding rail unit 14, a second guiding rail unit 15, and a mounting seat 13'. The first guiding rail unit 14 extends in the longitudinal direction (Y), and has opposite elongate lateral rail rods 141 spaced apart from each other in the transverse direction (X) in this embodiment. The second guiding rail unit 15 is mounted slidably on the first guiding rail unit 14, and includes two parallel elongate second rail rods 151 that extend in the transverse direction (X) and that are disposed spacedly between the lateral rail rods 141 of the first guiding rail unit 14, and two sliding blocks 152 (only one is shown) each interconnecting corresponding ends of the second rail rods 151. Each sliding block 152 has two engaging extensions 153 extending into and engaging slidably an engaging groove 142 in a corresponding lateral rail rod 141 such that each sliding block 152 is connected slidably to the corresponding lateral rail rod 141 of the first guiding rail unit 14. The mounting seat 13' is mounted slidably on the second rail rods 151 of the second guiding rail unit 15, and has parallel first and second connecting plates 134, 135 extending rearwardly and spaced apart from each other in the transverse direction (X) (see FIG. 8) in this embodiment. Each of the first and second connecting plates 134, 135 is formed with a through hole 1341, 1351 extending in the transverse direction (X), as best shown in FIG. 12.

The first drive unit 8 is mounted on the main frame 1' for driving the second guiding rail unit 15 to move along the driving lateral rail rods 141 of the first guiding rail unit 14 in the longitudinal direction (Y). In this embodiment, as shown in FIG. 8, the first drive unit 8 includes a bi-directional motor 81, a transmission wheel set 83, and a transmission belt unit. The bi-directional motor 81 has a motor shaft 82. The transmission wheel set 83 is disposed rotatably on the main frame 1', and is rotatable in response to operation of the bi-directional motor 81. The transmission belt unit includes a looped first transmission belt 84 trained on the transmission wheel set 83 and the motor shaft 82, and a second transmission belt 85 trained on the transmission wheel set 83 and having opposite ends 851 connected respectively to the second rail rods 151 of the second guiding rail unit 15.

Figure 10:
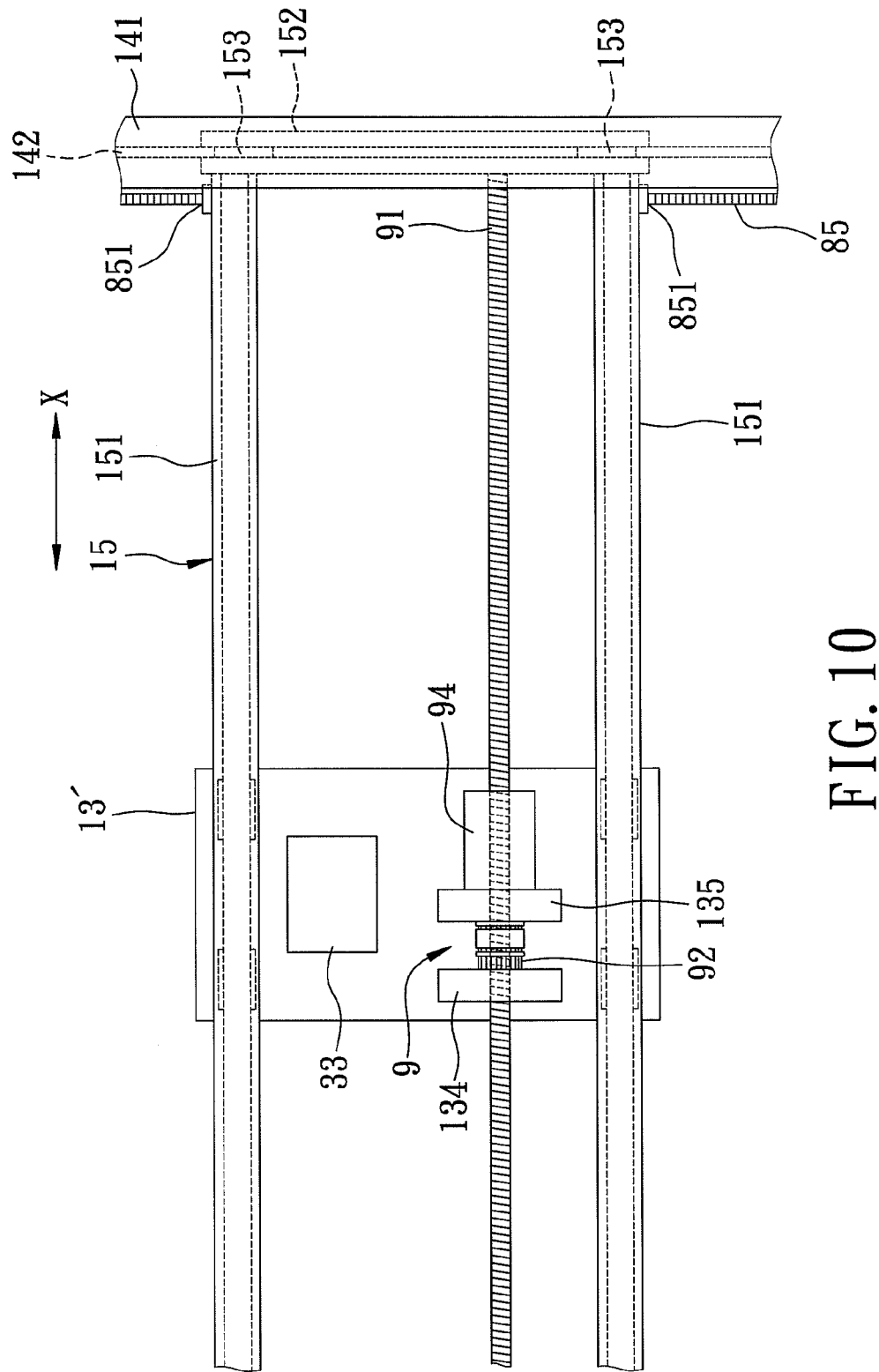
FIG. 10 is a fragmentary schematic rear view showing the fourth preferred embodiment.
Figure 11:
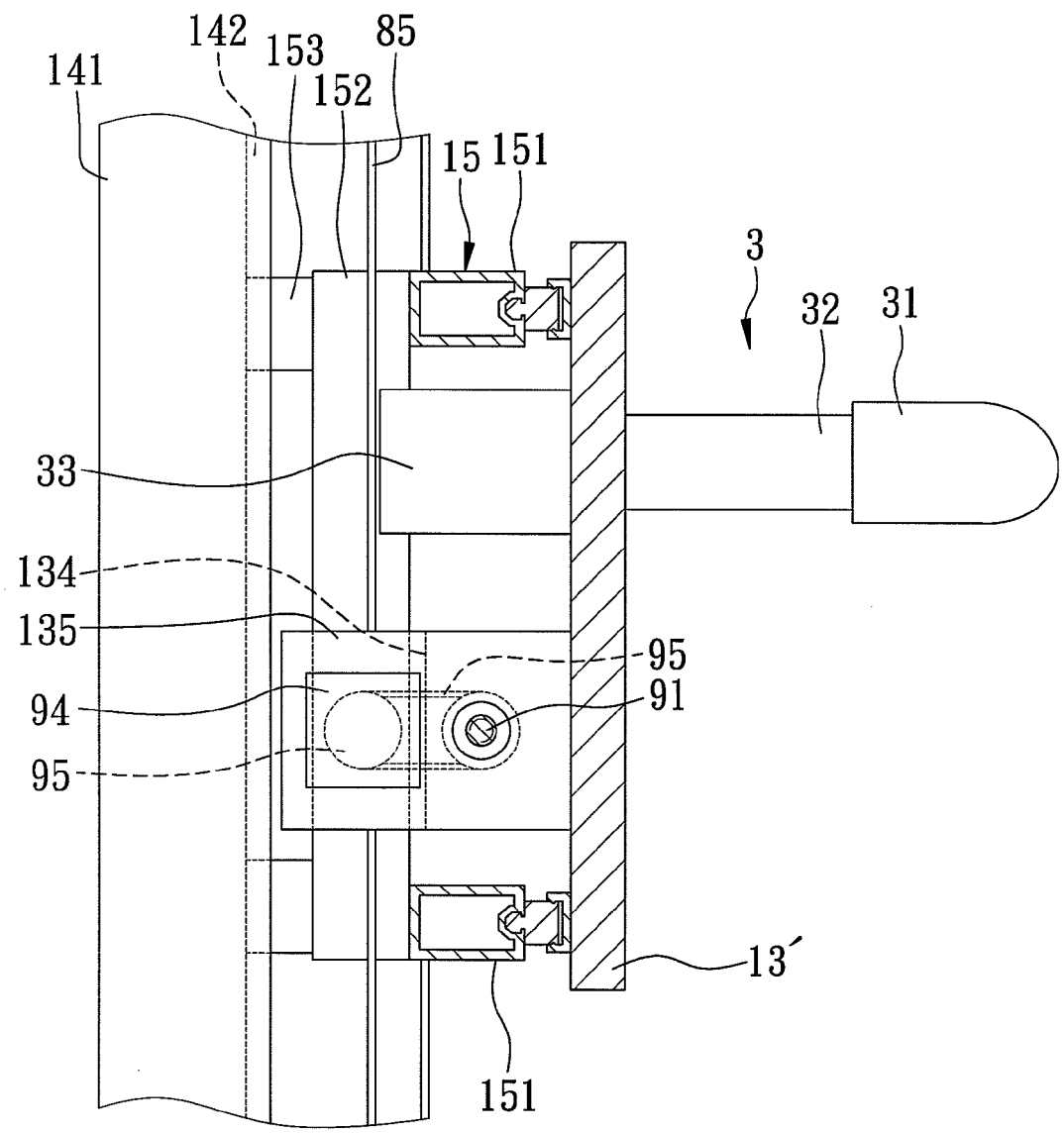
FIG. 11 is a fragmentary schematic sectional view of the fourth preferred embodiment taken along line XI-XI in FIG. 8.

The second drive unit 9 drives the mounting seat 13' to move along the second rail rods 151 in the transverse direction (X). In this embodiment, referring to FIGS. 10 to 12, the second drive unit 9 includes an elongate threaded rod 91, a transmission sleeve 92, two bearings 93, a bi-directional motor 94, and a looped transmission belt 95. The threaded rod 91 is mounted fixedly on the second guiding rail unit 15, extends in the transverse direction (X) through the through holes 1341, 1351 in the first and second connecting plates 134, 135 of the mounting seat 13', and is disposed between the second rail rods 151 of the second guiding rail unit 15. The transmission sleeve 92 is sleeved rotatably on and is connected threadedly to the threaded rod 91, and has opposite first and second end portions 921, 922 that extend respectively through the through holes 1341, 1351 in the first and second connecting plates 134, 135 of the mounting seat 13', and an intermediate gear portion 923 interconnecting the first and second end portions 921, 922, and disposed between and abutting against the first and second connecting plates 134, 135 of the mounting seat 13'. The bearings 93 are sleeved respectively on the first and second end portions 921, 922 of the transmission sleeve 92, and are disposed respectively in the through holes 1341, 1351 in the first and second connecting plates 134, 135 of the mounting seat 13'. The bi-directional motor 94 is mounted on the second connecting plate 135 of the mounting seat 13', and has a motor shaft 941. The transmission belt 95 is trained on the intermediate gear portion 923 of the transmission sleeve 92 and the motor shaft 941 of the bi-directional motor 94. The transmission sleeve 92 is rotatable relative to the threaded rod 91 in response to operation of the bi-directional motor 94 so as to move relative to the threaded rod 91 such that the intermediate gear portion 923 of the transmission sleeve 92 drives the mounting seat 13' to move in response to movement of the transmission sleeve 92.

The massage unit 3 is mounted on the mounting seat 13', and has the same configuration as that in the first preferred embodiment of FIG. 2.

The control unit 4' is connected electrically to the bi-directional motor 81 of the first drive unit 8, the bi-directional motor 94 of the second drive unit 9 and the motor 33 of the massage unit 3 for controlling the first drive unit 8, the second drive unit 9 and the motor 33 of the massage unit 3 so that the head portion 31 of the massage rod 32 is moved to a desired position through movement of the mounting seat 13' and the second guiding rail unit 15 so as to contact a user's body at a desired acupuncture point and that the motor 33 of the massage unit 3 drives the massage rod 32 to rotate at a desired speed.

The operating unit 5' is connected electrically to the control unit 4', and is operable so as to output a control signal to the control unit 4' such that the control unit 4' controls the bi-directional motor 81 of the first drive unit 8, the bi-directional motor 94 of the second drive unit 9, and the motor 33 of the massage unit 3 based on the control signal from the operating unit 5'.

In such a configuration, by controlling the first and second drive units 8 and 9, the head portion 31 of the massage rod 32 is movable in the transverse and longitudinal directions (X, Y) so as to contact the user's body at various acupuncture points, thereby resulting in a relatively wide massage area as compared to the abovementioned conventional massage chair.

Figure 13:
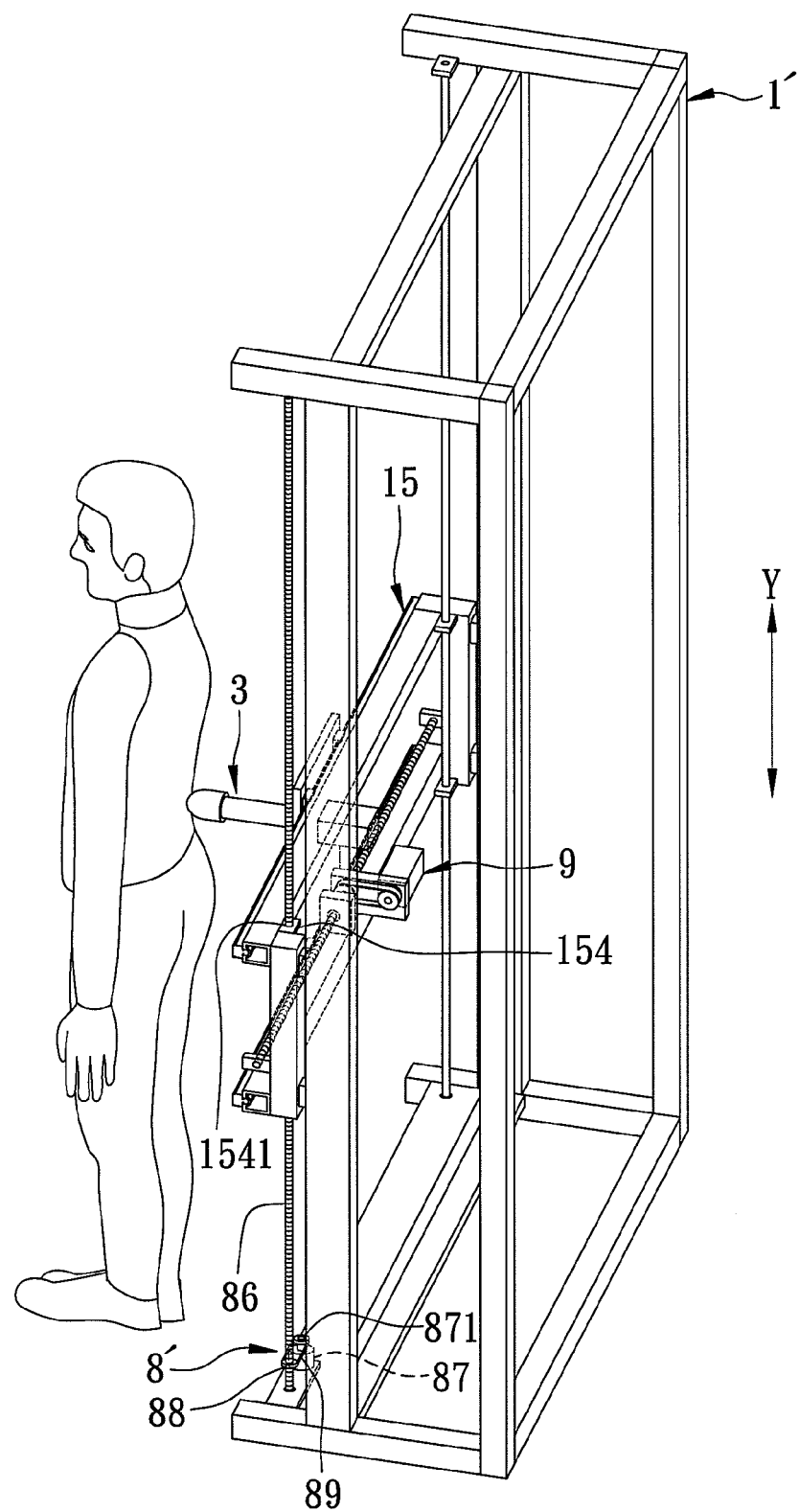
FIG. 13 is a perspective view showing the fifth preferred embodiment of a massaging apparatus according to the present invention.

FIG. 13 illustrates the fifth preferred embodiment of a massaging apparatus according to this invention, which is a modification of the fourth preferred embodiment. Unlike the fourth preferred embodiment, the second guiding rail unit 15' further has two connecting portions 154 (only one is shown) each formed with a threaded hole therethrough that extends in the longitudinal direction (Y).

In this embodiment, the first drive unit 8' includes an elongate threaded rod 86, a bi-directional motor 87, a transmission wheel 88, and a looped transmission belt 89. The threaded rod 86 is journalled on the main frame 1', extends in the longitudinal direction (Y) through the threaded holes 1541 in the connecting portions 154 of the second guiding rail unit 15. The threaded rod 86 is rotatable so as to drive movement of the second guiding rail unit 15 in response to rotation of the threaded rod 86. The bi-directional motor 87 is mounted on the main frame 1' and is connected electrically to and is controlled by the control unit, and has a motor shaft 871. The transmission wheel 88 is mounted on and is co-rotatable with the threaded rod 86, and is rotatable in response to operation of the bi-directional motor 87. The transmission belt 89 is trained on the transmission wheel 88 and the motor shaft 871 of the bi-directional motor 87.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A massaging apparatus comprising:
   a main frame including an upright guiding rail unit extending in a longitudinal direction, and a mounting seat mounted slidably on said guiding rail unit;
   a drive unit mounted on said main frame for driving said mounting seat to move along said guiding rail unit in the longitudinal direction;
   a massage unit mounted on said mounting seat and including a massage rod having a head portion, and a motor having an output shaft journalled on said mounting seat and connected to said massage rod for driving eccentric rotation of said massage rod relative to said output shaft; and
   a control unit connected electrically to said drive unit and said motor of said massage unit for controlling said drive unit and said motor of said massage unit so that said head portion of said massage rod is moved to a desired position through movement of said mounting seat so as to contact a user's body at a desired acupuncture point and that said motor of said massage unit drives said massage rod to rotate at a desired speed, wherein said drive unit includes
   a bi-directional motor connected electrically to and controlled by said control unit, and having a motor shaft journalled on said main frame;
   a transmission wheel set disposed rotatably on said main frame and rotatable in response to operation of said bi-directional motor; and
   a transmission belt trained on said transmission wheel set and said motor shaft of said bi-directional motor and having opposite ends connected to said mounting seat of said main frame.

2. The massage apparatus as claimed in claim 1, wherein:
   said guiding rail unit includes opposite elongate lateral rail rods spaced apart from each other in a transverse direction transverse to the longitudinal direction; and
   said mounting seat has opposite lateral sliding blocks each connected slidably to a corresponding one of the lateral rail rods of said guiding rail unit.

3. The massaging apparatus as claimed in claim 1, further comprising a thermal generating unit mounted to said main frame for radiating heat toward a user's body.

4. The massaging apparatus as claimed in claim 3, wherein said thermal generating unit includes at least one infrared heater disposed in said main frame for generating heat so as to heat air in said main frame, and at least one fan disposed in said main frame for blowing heated air out of said main frame toward the user's body.

5. A massaging apparatus comprising:
a main frame including
an upright first guiding rail unit extending in a longitudinal direction and having opposite elongate lateral rail rods spaced apart from each other in a transverse direction transverse to the longitudinal direction,
a second guiding rail unit mounted slidably on said first guiding rail unit, and including two parallel elongate second rail rods that extend in the transverse direction and that are disposed spacedly between said lateral rail rods of said first guiding rail unit, and
a mounting seat mounted slidably on said second rail rods of said second guiding rail unit;
a first drive unit mounted on said main frame for driving said second guiding rail unit to move along said lateral rail rods of said first guiding rail unit in the longitudinal direction;
a second drive unit for driving said mounting seat to move along said second rail rods in the transverse direction;
a massage unit mounted on said mounting seat and including a massage rod having a head portion, and a motor having an output shaft journalled on said mounting seat and connected to said massage rod for driving eccentric rotation of said massage rod relative to said output shaft; and
a control unit connected electrically to said first drive unit, said second drive unit and said motor of said massage unit for controlling said first drive unit, said second drive unit and said motor of said massage unit so that said head portion of said massage rod is moved to a desired position through movement of said mounting seat and said second guiding rail unit so as to contact a user's body at a desired acupuncture point and that said motor of said massage unit drives said massage rod to rotate at a desired speed.

6. The massaging apparatus as claimed in claim 5, wherein said second guiding rail unit further includes two opposite sliding blocks each interconnecting corresponding ends of said second rail rods and connected slidably to a corresponding one of said lateral rail rods of said first guiding rail unit.

7. The massaging apparatus as claimed in claim 5, wherein said first drive unit includes:
a bi-directional motor connected electrically to and controlled by said control unit, and having a motor shaft;
a transmission wheel set disposed rotatably on said main frame and rotatable in response to operation of said bi-directional motor; and
a transmission belt unit including a looped first transmission belt trained on said transmission wheel set and said motor shaft of said bi-directional motor, and a second transmission belt trained on said transmission wheel set and having opposite ends connected respectively to said second rail rods of said second guiding rail unit.

8. The massaging apparatus as claimed in claim 5, wherein:
said mounting seat has parallel first and second connecting plates spaced apart from each other in the transverse direction, each of said first and second connecting plates being formed with a through hole extending in the transverse direction; and
said second drive unit includes
an elongate threaded rod mounted fixedly on said second guiding rail unit, extending in the transverse direction through said through holes in said first and second connecting plates of said mounting seat, and disposed between said second rail rods of said second guiding rail unit,
a transmission sleeve sleeved rotatably on and connected threadedly to said threaded rod, and having opposite first and second end portions that extend respectively through said through holes in said first and second connecting plates of said mounting seat, and an intermediate gear portion interconnecting said first and second end portions, and disposed between and abutting against said first and second connecting plates of said mounting seat,
two bearings sleeved respectively on said first and second end portions of said transmission sleeve, and disposed respectively in said through holes in said first and second connecting plates of said mounting seat,
a bi-directional motor mounted on said second connecting plate of said mounting seat, connected electrically to and controlled by said control unit, and having a motor shaft, and
a looped transmission belt trained on said intermediate gear portion of said transmission sleeve and said motor shaft of said bi-directional motor,
said transmission sleeve being rotatable relative to said threaded rod in response to operation of said bi-directional motor so as to move relative to said threaded rod such that said intermediate gear portion of said transmission sleeve drives said mounting seat to move in response to movement of said transmission sleeve.

9. The massage apparatus as claimed in claim 5, wherein:
said second guiding rail unit further has a connecting portion formed with a threaded hole therethrough that extends in the longitudinal direction; and
said first drive unit includes
an elongate threaded rod journalled on said main frame, extending in the longitudinal direction through said threaded hole in said connecting portion of said second guiding rail unit, and connected threadedly to said connecting portion of said second guiding rail unit, said threaded rod being rotatable so as to drive movement of said second guiding rail unit in response to rotation of said threaded rod,
a bi-directional motor connected electrically to and controlled by said control unit, and having a motor shaft,
a transmission wheel mounted on and co-rotatable with said threaded rod, and rotatable in response to operation of said bi-directional motor, and
a looped transmission belt trained on said transmission wheel and said motor shaft of said bi-directional motor.

10. A massaging apparatus comprising:
a main frame including an upright guiding rail unit extending in a longitudinal direction, and a mounting seat mounted slidably on said guiding rail unit;
a drive unit mounted on said main frame for driving said mounting seat to move along said guiding rail unit in the longitudinal direction;
a massage unit mounted on said mounting seat and including a massage rod having a head portion, and a motor having an output shaft journalled on said mounting seat and connected to said massage rod for driving eccentric rotation of said massage rod relative to said output shaft; and
a control unit connected electrically to said drive unit and said motor of said massage unit for controlling said drive unit and said motor of said massage unit so that said head portion of said massage rod is moved to a desired position through movement of said mounting seat so as to contact a user's body at a desired acupuncture point and that said motor of said massage unit drives said massage rod to rotate at a desired speed, wherein said mounting seat has a connecting portion formed with a threaded hole therethrough that extends in the longitudinal direction, and wherein said drive unit includes
- an elongate threaded rod journalled on said main frame, extending in the longitudinal direction through said threaded hole in said connecting portion of said mounting seat, and connected threadedly to said connecting portion of said mounting seat, said threaded rod being rotatable relative to said main frame so as to drive movement of said mounting seat in response to rotation of said threaded rod,
- a bi-directional motor connected electrically to and controlled by said control unit, and having a motor shaft,
- a transmission wheel mounted on and co-rotatable with said threaded rod, and
- a looped transmission belt trained on said transmission wheel and said motor shaft of said bi-directional motor.

11. The massage apparatus as claimed in claim 10, wherein:
- said guiding rail unit includes opposite elongate lateral rail rods spaced apart from each other in a transverse direction transverse to the longitudinal direction; and
- said mounting seat has opposite lateral sliding blocks each connected slidably to a corresponding one of the lateral rail rods of said guiding rail unit.

12. The massaging apparatus as claimed in claim 10, further comprising a thermal generating unit mounted to said main frame for radiating heat toward a user's body.

13. The massaging apparatus as claim in claim 12, wherein said thermal generating unit includes at least one infrared heater disposed in said main frame for generating heat so as to heat air in said main frame, and at least one fan disposed in said main frame for blowing heated air out of said main frame toward the user's body.

* * * * *